(12) United States Patent
Bain et al.

(10) Patent No.: US 6,824,385 B1
(45) Date of Patent: Nov. 30, 2004

(54) DENTAL SYRINGE APPARATUS AND METHOD

(75) Inventors: Don Bain, Aldergrove (CA); Dave Skipp, Abbotsford (CA)

(73) Assignee: Dentech Corporation, Lynden, WA (US)

( * ) Notice: Subject to any disclaimer, the term of this patent is extended or adjusted under 35 U.S.C. 154(b) by 77 days.

(21) Appl. No.: 10/430,660

(22) Filed: May 5, 2003

(51) Int. Cl.[7] .............................................. A61C 17/02
(52) U.S. Cl. ............................ 433/80; 433/85; 604/33
(58) Field of Search ............................ 433/80, 98–100, 433/88, 126, 84, 85; 251/229, 237–241; 604/30, 33, 43, 93.01, 118, 146, 147, 173, 181, 236, 246, 249, 23, 26; 128/DIG. 12

(56) References Cited

U.S. PATENT DOCUMENTS

| | | | | |
|---|---|---|---|---|
| 2,362,608 A | * | 11/1944 | Allen | 251/229 |
| 4,026,025 A | * | 5/1977 | Hunt | 433/80 |
| 4,149,315 A | * | 4/1979 | Page et al. | 433/114 |
| 4,619,612 A | * | 10/1986 | Weber et al. | 433/80 |
| 4,957,483 A | * | 9/1990 | Gonser et al. | 604/30 |
| 5,045,055 A | | 9/1991 | Gonser et al. | 604/33 |
| 5,125,835 A | | 6/1992 | Young | 433/80 |
| 5,199,871 A | | 4/1993 | Young | 433/80 |
| 5,234,338 A | | 8/1993 | Young | 433/80 |
| 5,848,893 A | | 12/1998 | Martin | 433/80 |
| 6,293,792 B1 | | 9/2001 | Hanson | 433/80 |

* cited by examiner

Primary Examiner—Melba Bumgarner
(74) Attorney, Agent, or Firm—Holland & Hart (57) ABSTRACT

A medical syringe contains neoprene O-rings and is constructed such that its nozzle and handle can be sterilized without damaging the O-rings. A hollow aluminum handle provides a first handle opening at the bottom and a second handle opening at the top. An insert is removably inserted through the second handle opening to locate the insert at the top of the aluminum handle. An elongated metal or plastic valve body is removably inserted into the first handle opening to locate a top end of the valve body and two normally closed valves adjacent to the insert, and to locate a bottom end of the valve body at the first handle opening. The bottom end of the valve body is hose-connected to an air and a water pressurized source. Each valve includes a valve seat and a valve O-ring that is spring-biased against the valve seat. Two valve actuators in the insert selectively open the two valves by moving the valve O-rings away from the valve seats. The valve actuators are short curved rods that are guided by the insert so as to move about a virtual center of rotation. An elongated cavity within the insert contains O-rings and releasably mounts one end of an elongated nozzle. Manual removal of the valve body allows the handle body, complete with nozzle, insert, and release ring to be sterilized without compromising the structural integrity of the neoprene O-rings in the valve body. In addition, the nozzle can also be removed from the handle body to facilitate the separate sterilization of the nozzle.

19 Claims, 5 Drawing Sheets

DENTAL SYRINGE APPARATUS AND METHOD

FIELD OF THE INVENTION

This invention relates to the field of dentistry, and more specifically to orthodontics syringe apparatus of the type having a handle at one end and having an intra-oral nozzle at the other end.

BACKGROUND OF THE INVENTION

Hand-held syringes that control the flow of a liquid and/or air into a body cavity such as the oral cavity are known. Typically, such a syringe is an L-shaped device having a handle, a nozzle, and one or more finger-actuated valves that are spring-biased closed, and whose operation controls the outward flow of liquid and/or air from the nozzle, with the handle being connected to one or more flexible and under-pressure fluid/air supply hoses. Often these valves are the well known Schrader valves of the type used in pneumatic tire stems. In this way, fluid, air, or a mixture of fluid and air can be selectively discharged from the nozzle. The following United States patents are examples of known prior devices. These patents are incorporated herein by reference.

U.S. Pat. No. 5,045,055 provides a medical/dental syringe that includes an elongated handle having a nozzle connected to one thereof, and having a two-hose assembly connected to the other end thereof. The handle includes a valve body head, two flow-control valves, and two finger actuators for the flow-control valves, to thus selectively control the flow of water, air, or both water and air from the nozzle. The two flow-control valves, and their O-rings, are removable to facilitate periodic replacement. The use of VITON-brand O-rings is suggested in order to resist the effect of repeatedly subjecting the O-rings to high temperature. Automatic valves within the two-hose assembly operate to seal the water hose and the air hose when the two-hose assembly is disconnected from the handle.

U.S. Pat. No. 5,125,835 provides a retainer assembly for detachably mounting the multiple-conduit tip of a syringe onto a syringe head by way of a spring-biased locking collar. The tip includes an annular groove that receives a plurality of ball elements when the tip is inserted into the syringe head. A movable and spring-biased collar that is carried by the syringe head retains the ball elements within the tip's groove, thus removably mounting the tip on the syringe head.

U.S. Pat. No. 5,199,871 provides a control valve for a dental syringe. The control valve, having a finger-actuator, is mechanically locked in a passageway that is provided within a syringe-head by the operation of an O-ring that expands into a groove that is provided in the wall of the passageway.

U.S. Pat. No. 5,234,338 provides an autoclavable head and handle for a dental syringe wherein the entire external housing, including the handle, can be removed from utility supply lines, so that the external surfaces of the housing can be autoclaved. This function is facilitated by providing a substantially internal quick-disconnect mechanism or cartridge whereby the flow of air and water to the syringe is discontinued, such that the syringe's handle, head and tip can be steam-sterilized.

U.S. Pat. No. 5,848,893 provides that a syringe's shutoff valves are mechanically retained in place within a syringe head by way of a retaining pin that seats within a groove that is contained within each of the shutoff valves, this retaining pin entering the groove when that valve's inlet hose barb is screw-mounted onto the syringe head. In addition, the syringe nozzle is retained in an adapter that screw-mounts to the syringe head by way of a resilient snap-ring that encircles the nozzle and sits within a groove that is formed in the nozzle.

U.S. Pat. No. 6,293,792 is similar to above-mentioned '835 patent wherein the ball-activated quick-tip-connect mechanism is constructed so as to also seat the balls of the quick-connect mechanism in radially-placed indentations that are carried by the tip. In this way the balls additionally provide structural interference against rotation of the tip.

SUMMARY OF THE INVENTION

The present invention provides a new and useful dental syringe that is constructed and arranged such that the internal portions of the syringe that contain O-rings, or at least the portion of the syringe that contains valve-associated O-rings, can be removed from the syringe prior to the syringe being sterilized, as by autoclaving. Thus, all O-rings that function within the syringe, or at least the O-rings that function within the syringe's valves, are constructed of a material such as neoprene that would likely be damaged by autoclaving.

In order to provide an aesthetically pleasing and nicely weight-balanced syringe, the syringe of this invention includes (1) an internal and top-located insert, which could be made of metal, plastic, or any other suitable material, to contain flow-channels and the like that are required to accommodate air and/or water flow between the syringe's two valves and the syringe's nozzle, (2) a generally hollow and light-weight metal handle-body at whose upper end a nozzle and the insert are located, and (3) an internally-located and elongated light-weight, metal, and manually-removable valve body that extends internally the length of the handle body, so as to locate the syringe's two valves at the upper end of the handle body and generally adjacent to and beneath the insert, and so as to locate two hose barbs at the bottom of the handle body.

This construction and arrangement wherein the syringe's two normally-closed valves are placed at the top of a removable valve body whose bottom area contains two hose barbs to which water and air supply hoses are connected provides that when this valve body is manually removed or disconnected from the syringe, the syringe's two normally-closed valves are removed with the valve body, and the two hoses are disconnected from the syringe, thus providing a removed valve body in which the two supply hoses are scaled by operation of the two normally-closed valves.

When assembling the syringe of the present invention, the syringe's insert is first inserted into an upper portion of the handle body. An insert assembly pin is then inserted into an opening that is provided in an upper portion of the handle body. This insert assembly pin penetrates an opening in the insert, and thereby secures the insert within the handle body. Two side-by-side located, virtual-center-movable, and semi-circular valve actuating rods are carried by the insert, and this first assembly step places the top end of these two virtual-center valve actuating rods in positional cooperation with two O-ring-retained valve actuating buttons that are inserted into two side-by-side holes that are located on an upper inclined surface of the handle body.

As a second assembly step, the valve body is inserted into an opening that is located at the bottom of the handle assembly. This second assembly step places a normally-closed air valve and a normally-closed water valve that are located at the top of the handle member under the insert, and in positional cooperation with the bottom end of the two valve actuating rods. The two curved valve actuating rods enable the linear direction of movement of the two buttons to be inclined to the linear direction of movement of the two valves.

As a third assembly step, a lock pin is inserted into an opening that is provided in the upper portion of the handle assembly. This lock pin is adapted to enter an O-ring-containing groove that is provided in a spigot or post that is carried at the top of the valve body. As will be apparent from the following description, the lock pin and a release ring together lock the valve body in the handle body.

The syringe's nozzle is connected to a manually rotatable release ring that encircles the outer diameter (OD) of the nozzle. The release ring is secured to the nozzle by way of a coiled torsion spring, one end of which is retained by the release ring. The coil of this torsion spring grips the outer diameter (OD) of the nozzle. That is, the inner diameter (ID) of the torsion spring is somewhat smaller than the OD of the nozzle. The release ring is secured to the body of the syringe by an assembly pin.

When assembling the release ring and the nozzle, one end of the torsion spring is retained by the release ring, and the torsion spring is then rotated against its wound direction, to thereby produce a spring ID that is larger than the nozzle OD. With the spring held in this larger ID state, the nozzle is now inserted into the center of the release ring, and the release ring is placed at a desired location along the length of the nozzle. The torsion spring is now released, whereupon the ID of the torsion spring decreases, thereby causing the release ring to be rotatably mounted at this desired position on the OD of the nozzle.

As a fourth assembly step, the release ring is secured to the body of the syringe with the assembly pin. The release ring presses against the lock pin and locks the valve body in the handle.

As the fifth and final assembly step, an end of the nozzle is inserted into the release ring by rotating the release ring thereby unwinding the torsion spring so as to facilitate inserting the nozzle within the release ring and torsion spring. The release ring and torsion spring can then be released thereby securing the nozzle to the release ring. Later, when it is desired to disconnect the valve body from the syringe, the above-mentioned release ring is rotated about 30 degrees around the nozzle. This rotation of the release ring coils the torsion spring, such that upon a subsequent release of the valve body, the release ring returns to its home position. This rotation of the release ring also brings a recessed portion of the release ring into positional coincidence with the above-mentioned lock pin. The above-mentioned O-ring that was compressed by the lock pin now operates to push the lock pin out of the above-mentioned groove in the spigot that is located at the top of the valve body, the valve body is no longer locked by the lock pin, and the valve body can now be pulled downward and out of the handle body. Note that since the top of the valve body carries normally closed valves, the supply hoses that are connected to the bottom of the valve body remain sealed.

As above described, syringes in accordance with this invention include two top-located and finger-operated buttons that, when pressed, selectively provide for the supply of pressurized air and/or water to the syringe's nozzle. In accordance with the invention, a new and unusual virtual-center actuator rod extends between the bottom of these two buttons and the top of an associated valve, so as to translate a linear force that is applied to a button into a linear valve-opening force that is applied to an associated valve. These two virtual-center actuator rods are arranged such that the direction of linear movement of each button extends at an angle to the direction of linear movement of the associated valve.

DETAILED DESCRIPTION OF THE INVENTION

Figure 1:
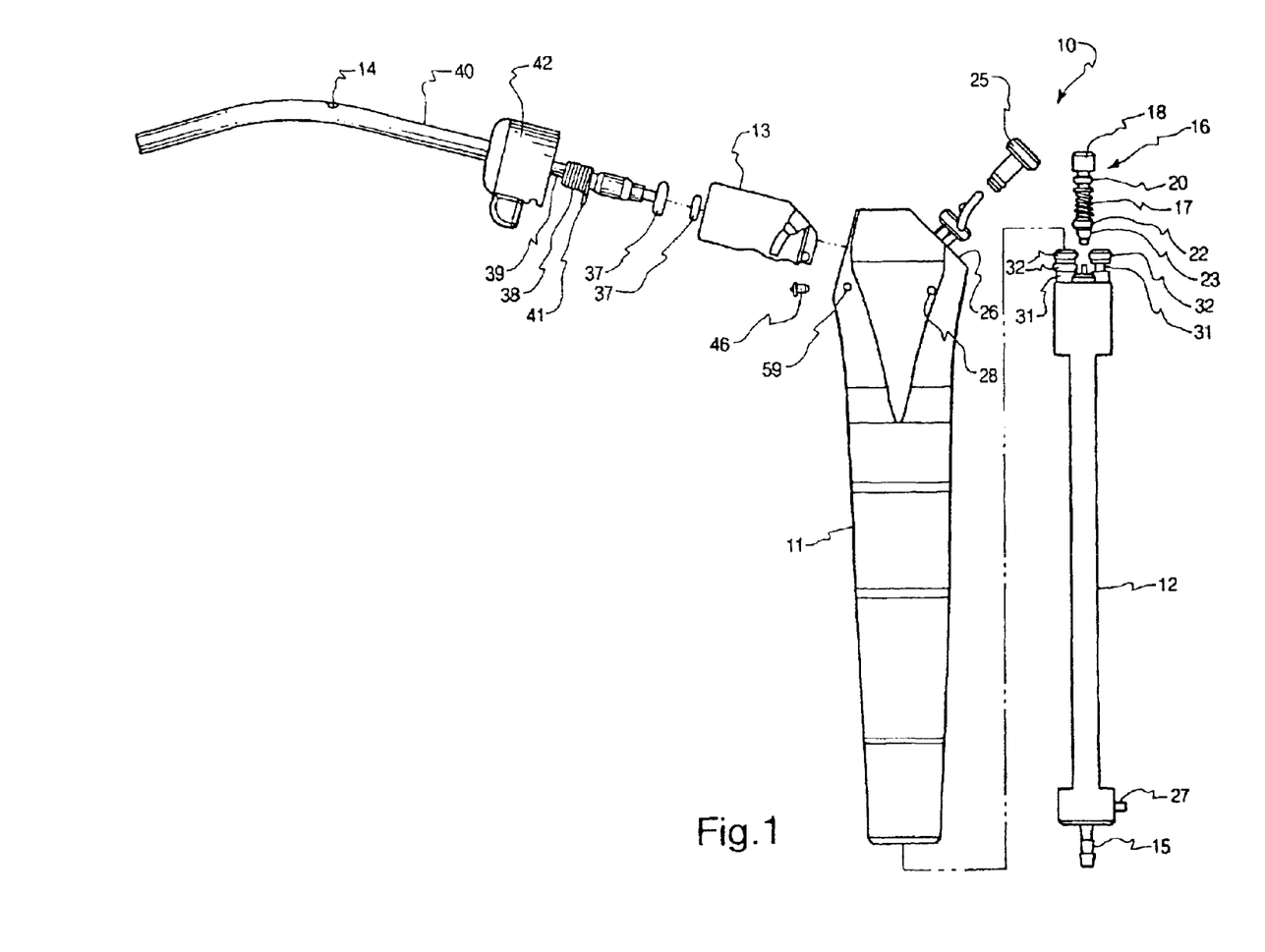
FIG. 1 is an exploded side view showing a syringe in accordance with the invention.

With reference to FIG. 1, reference number 10 designates a generally L-shaped dental syringe in accordance with the invention.

Syringe 10 includes a hollow handle body 11 that is preferable formed of aluminum, an elongated valve body 12 preferably formed of brass, plastic, or steel that is upward-insertable into the open bottom of handle body 11, an internally-located insert 13 preferably formed of brass that is located at the top of handle body 11, and a nozzle 14 preferably formed of a metal such as stainless steel that extends generally 105-degrees outward from the top of handle 11. It should be noted that alternative embodiments of straight syringes with nozzles that extend approximately 180 degrees from the top of the handle 11 also fall under the teachings of this application.

After insert 13 has been manually inserted into an opening that is provided at the top portion of handle body 11, insert 13 is secured in this inserted position by the operation of a manually removable insert assembly pin 28. The insert 13 is preferably composed of either metal or plastic.

The bottom end of valve body 12 includes two side-by-side located hose barbs 15, one of which is adapted to receive a hose and a shut-off valve (not shown) that is connected to a source of pressurized air, and the other of which is adapted to receive a hose and a shut-off valve (not shown) that is connected to a source of pressurized water.

Figure 4:
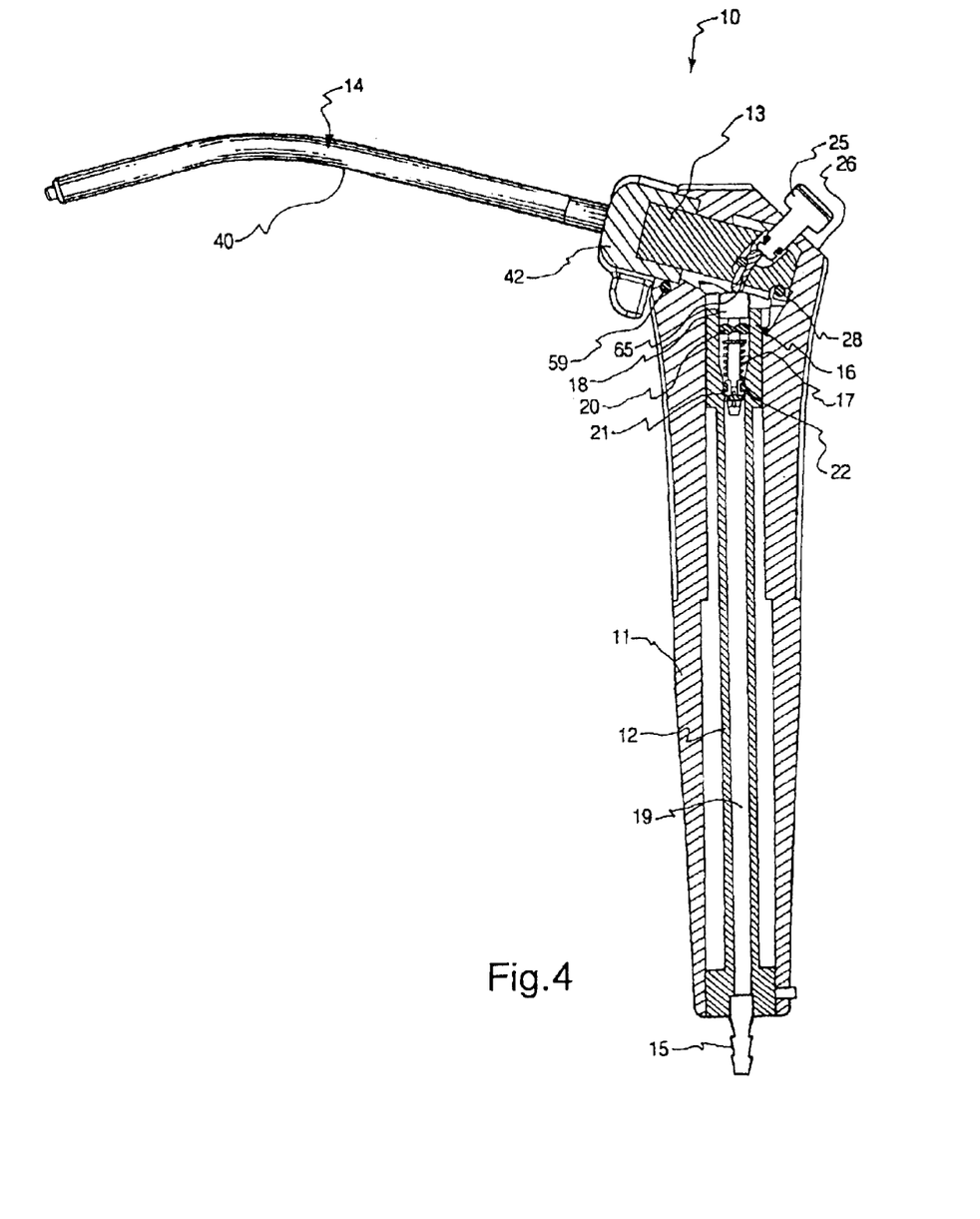
FIG. 4 is a vertical section view of the FIG. 1 syringe, this section view being taken in a plane that lies forward of the plane of FIG. 2, FIG. 4 showing the construction and arrangement of one of the two valves that respectively control the flow of air and/or water to the nozzle.
Figure 5:
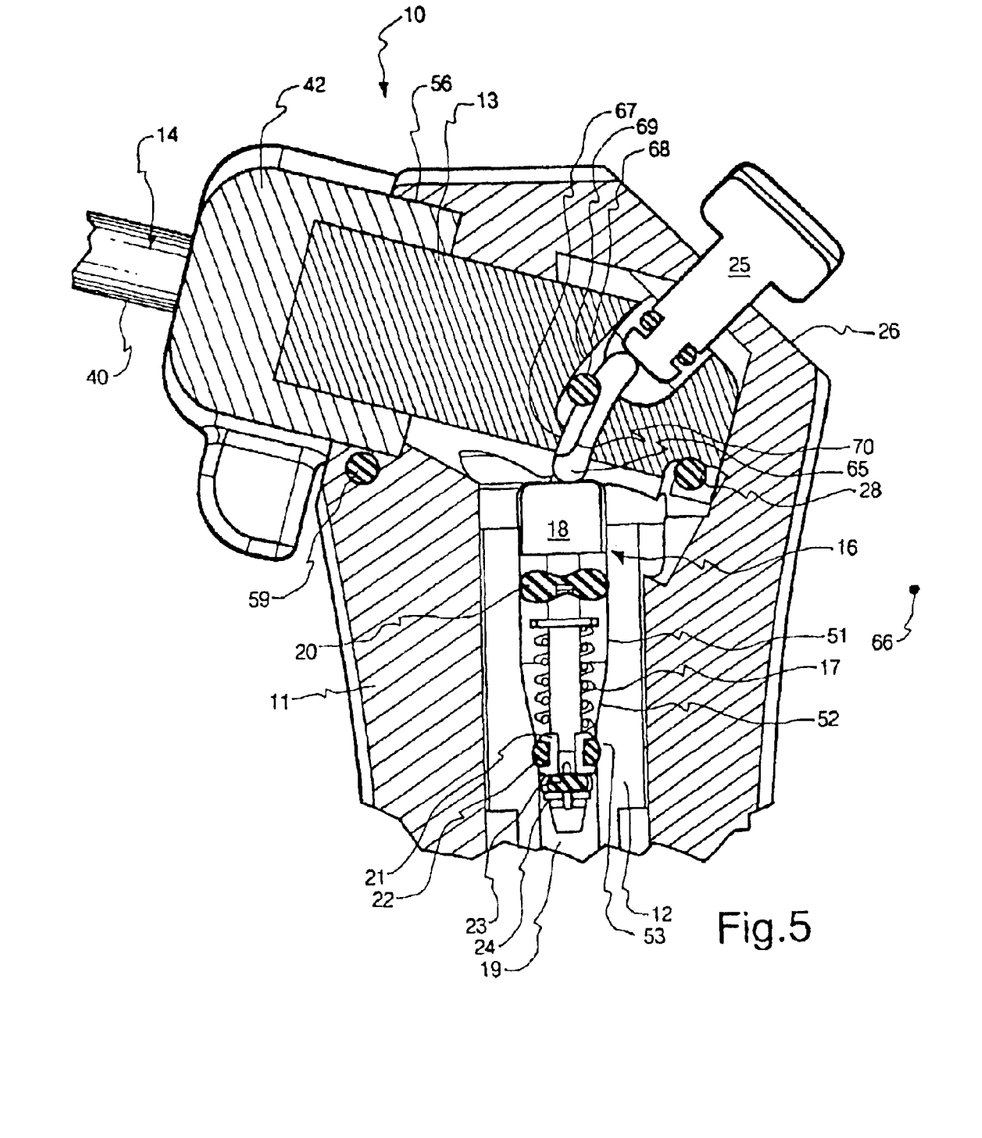
FIG. 5 is an enlarged view of the upper portion of FIG. 4.

Valve body 12 also includes two internal and upward-extending flow channels 19, one channel 19 of which is shown in FIGS. 4 and 5. The bottom end of each of these two internal flow channels 19 connects to an individual one of the two hose barbs 15, and the top end of each of these two internal flow channels 19 terminates at, and is closed by, an individual one of the two normally-closed valves 16 (best seen in FIGS. 4 and 5), one valve 16 of which is shown in an exploded position in FIG. 1. Each of the two valves 16 is spring-biased to a closed position by the operation of a coil spring 17 that encircles a metal valve stem 18, and each of the two valves 16 includes a valve stem O-ring 20, a valve seat 21 (best seen in FIG. 5), and a valve O-ring 23 (best seen in FIG. 5).

While not a limitation on the spirit and scope of this invention, the unique construction and arrangement of syringe 10 advantageously enables the use of neoprene O-rings throughout syringe 10, or at least throughout the valves that are contained within syringe 10.

As a feature of the invention, a C-clip 24 as shown in FIG. 5 is installed in each of the two valves 16 such that valve stem 18 and its various attachments, including valve seat 21 and valve seat O-ring 22, can be forcibly extracted from valve body 12 for maintenance.

With reference to FIG. 5, each of the two valve assemblies 16 is inserted downward into an oversize or relatively large diameter hole 51 that is formed in the top of valve body 12, thus allowing valve seat O-ring 22 to pass the cross drilled holes 71 72 (shown in FIG. 3) without being damaged. Moreover, a tapered-diameter portion 52 at the bottom of hole 51 is provided to compress valve seat O-ring 22 within valve body 12 in a gradual manner, as valve seat O-ring 22 reaches its final position whereat O-ring 22 settles into an annular groove 53 that is formed in the bottom portion of hole 51.

The bottom end of valve body 12 includes an alignment pin 27 that extends outward therefrom. The positioning of alignment pin 27 ensures the correct physical position of valve body 12 within handle body 11. The stop pin 74 extends up from the valve body 12 between the two spigots 31 into a matching cavity in the valve insert 13 best shown in FIG. 3.

Figure 3:
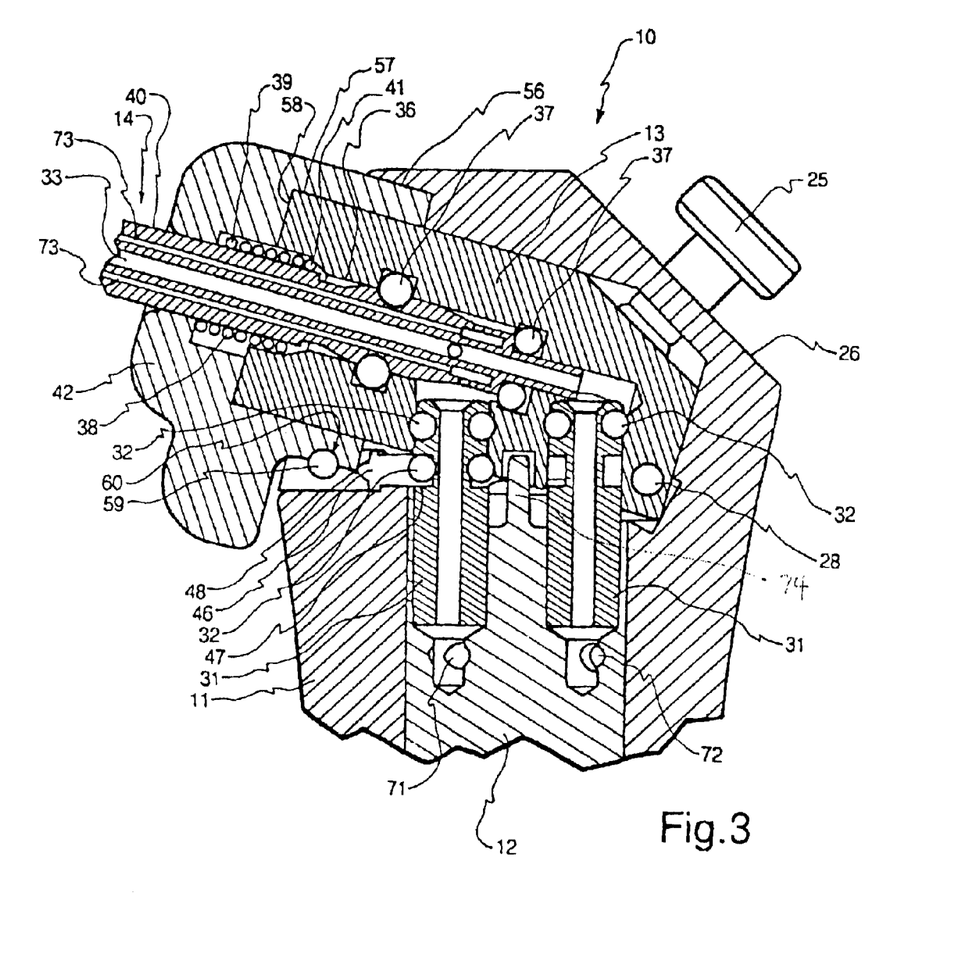
FIG. 3 is an enlarged view of the upper portion of FIG. 2.

The top end of valve body 12 (the spigots 31) and the mating interior surface of the insert 13 are preferably machined to provide an o-ring 32 seal so that air and water does not leak downward through valve 16 (shown in FIG. 1) when one or more of these valves are opened as shown in FIG. 3. The fluid flows up through the cross drilled holes 71 72 shown in FIG. 3. The spigots 31 carry the fluids up into the insert 13 where o-rings 37 keep the water and air separate while they transfer from the insert onto the separate concentric passages in the nozzle. With valve body 12 correctly inserted within handle body 11, the two side-by side located valves 16 that are located on the upper end of valve body 12 are correctly aligned with the physical position of two side-by-side located push buttons 25 that are carried by the top inclined surface 26 of handle body 11, this button/valve aligned position being best seen in FIGS. 4 and 5.

Figure 2:
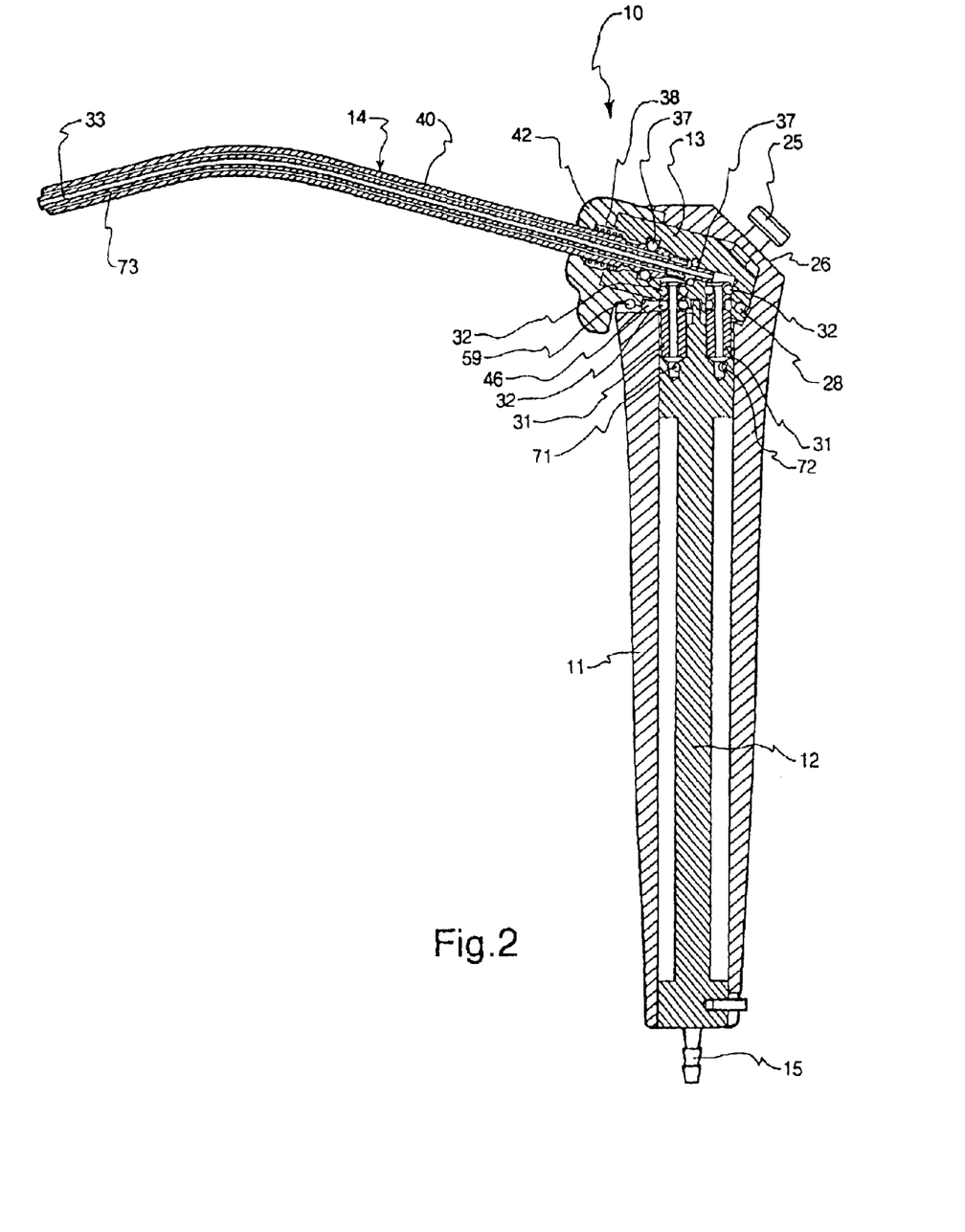
FIG. 2 is a vertical section view of the FIG. 1 syringe wherein the section view is taken in a centrally located plane that produces center-sectioning of the syringe's nozzle.

The top end of valve body 12 carries two metal spigots or posts 31 that individually carry a number of O-rings 32, as is best seen in FIGS. 2 and 3.

In addition, and as is best seen in FIGS. 1, 2 and 3, a lock pin 46 operates to lock valve body 12 in its inserted position. Lock pin 46 slideably extends through a hole that is provided in handle body 11, and the end of lock pin 46 is adapted to extend into an O-ring-containing groove 47 that is formed in a spigot 31.

When lock pin 46 is pushed to the right, as seen in FIG. 3, the end of lock pin 46 operates to compress the O-ring 32, as lock pin 46 is held in this pushed-position within groove 47 by an edge 48 of release ring 42.

With reference to FIG. 3, when release ring 42 is manually rotated (as will be described below), a recessed cam surface (not shown) that is machined into the edge 48 of release ring 42 is brought into alignment with lock pin 46. The O-ring 32 that is within groove 47 now expands and pushes lock pin 46 to the left, out of groove 47, as the left end of lock pin 46 is pushed into this recessed cam surface.

With lock pin 46 in this left-ward position, where the right end of lock pin 46 is no longer within groove 47, valve body 12 can be forcibly pulled out of handle body 11.

The insert 13 is machined to facilitate transferring the air and water from the spigots 31 to the separate concentric passages 33, 73 in the nozzle.

With reference to FIGS. 1–3, the right end of nozzle 14 is releaseably mounted in an elongated linear cavity 36 that is formed in insert 13, this releasable mounting being facilitated by the wound torsion spring 38, as is best seen in FIG. 3.

The torsion spring 38 has its left end 39 rotationally constrained by release ring 42, and has its right end 41 secured in a similar fashion to the insert 13, such that forcible rotation of the release ring 42 uncoils the wound spring 38 and allows the nozzle 14 to be inserted. When the force rotating the release ring 42 is removed the torsion spring 38 acts to return to its coiled position forcing the release ring 42 back to its home position. As the torsion spring 38 recoils, its ID is reduced claming the nozzle 14 and holding it in place axially and to a lesser extent rotationally.

The relaxed ID of torsion spring 38 is somewhat smaller than the OD surface 40 of nozzle 14. When release ring 42 is in its not-rotated or home position, as seen in FIG. 3, torsion spring 38 relatively tightly grips the OD surface 40 of nozzle 14.

In an operation to manually remove valve body 12 from handle body 11, manual rotation of release ring 42 for about 30 degrees allows the lock pin 46 for the valve body 12 to retract into the chamber on the outer edge of the release ring 42 thereby releasing the valve body 12. In addition, the rotation of the release ring 42 30 degrees also causes the nozzle 14 to release. The ability to release both the nozzle 14 and the valve body 12 with a rotation of the release ring 42 is a design feature that simplifies operation of the syringe and manufacturing. With release ring 42 held in this 30-degree-rotated position, lock pin 46 moves to the left in FIG. 3, the right end of lock pin 46 is thus withdrawn from groove 47, and valve body 12 can be manually pulled out of the bottom of handle body 11.

That is, release ring 42 functions in its 30-degree-rotated position to cause lock pin 46 to be withdrawn from the groove 47 that is formed in a spigot 31 that is carried at the top of valve body 12, to thus enable valve body 12 to be manually withdrawn from handle body 11.

As perhaps best seen in FIG. 3, release ring 42 sits in an opening 56 that is formed at the side and top of handle body 11. The ID of release ring 42 freely rotates on the OD 57 of insert 13, and the inside face of release ring 42 freely rotates on the front face 58 of insert 13.

Release ring 42 is secured to handle body 11 by a release ring assembly pin 59 which is held by handle body 11 and which mates with a U-shaped groove 60 that is formed in a portion of the OD surface of release ring 42.

One end of U-shaped groove 60, which can be called the home position end, cooperates with release ring assembly pin 59 to act as a home-stop for release ring 42, as torsion spring 38 operates to hold this end of U-shaped groove 60 against release ring assembly pin 59.

When release ring 42 is rotated about 30 degrees, as above described, the opposite end of U-shaped groove 60 engages release ring assembly pin 59 and acts as a rotation-stop that prevents damage to torsion spring 38. It should be noted that in reality the valve body 12 is effectively released when the release ring 42 is rotated only 7 degrees and the remainder of the rotation is to allow the ring to unwrap enough to release the nozzle 14. Likewise, the syringe can be manufactured so as to allow the valve body 12 and or the nozzle 14 to effectively release at almost any angle of rotation of the release ring 42.

As described, the above-mentioned 30 degree rotation of release ring 42 enables valve body 12 to be manually removed from handle body 11. With reference to FIG. 3, this 30 degree rotation of release ring 42 additionally uncoils the tension spring 38 such that the nozzle 14 can be removed from the insert 13.

That is, when release ring 42 is in its home position, lock pin 46 operates to lock valve body 12 in handle body 11, and release ring assembly pin 59 operates to lock release ring 42 to handle body 11. However, when release ring 42 is in its 30 degree rotated position, both valve body 12 and nozzle 14 can be manually removed from handle body 11.

The construction and arrangement of syringe 10 facilitates the removal of valve body 12 and its two top-located valves 16 by providing that the two valves 16 are actuated remotely and by forces that extend at an angle to the direction of linear movement of the two valve stems 18.

In order to optimize this remote valve operation by buttons 25, and in order to achieve the lightest possible button action or force, the invention provides an actuate-shaped or semi-circular shaped actuating rod 65 for each of the button/valve pairs, as is best seen in FIGS. 4 and 5.

In accordance with the invention, the semi-circular movement of each of the two actuating rods 65 is about a virtual-center-of-rotation that is indicated as virtual-center 66 in FIG. 5.

Since the semi-circular movement of actuating rods 65 occurs about this theoretical rotational center 66, the construction and arrangement of the invention places no physical limitations on the location of virtual-center 66, and the actuating rods 65 can operate through a range of angles, and can provide a range of forces-ratios, with very little accompanying friction.

This end result is accomplished by placing each of the two semi-circular actuator rods 65 in a semi-circular track 67 that is formed in insert 13. Preferably each of the two actuator rods 65 is supported and retained in its semi-circular track 67 by one or more metal ball bearings 68 that run in a recess 69 that is formed in each of the semi-circular tracks 67 and a corresponding recess 70 that is formed in each of the two actuator rods 65.

The length of the semi-circular movement of each of the two actuator rods 65 about virtual center 66 (for example about 30 degrees) is limited by ball bearing 68 engaging the end of one or both of the two semi-circular recesses 69 and 70, and in FIG. 5 it is seen that while ball bearing 68 has engaged the top end of recess 70, further downward movement of actuator rod 65 is possible, until ball bearing 68 engages the bottom end of recess 69.

In accordance with the spirit and scope of the invention, and particularly when friction is not a concern, any other form of actuator rod support, including but not limited to disc, roller, or tongue-and-groove, that is capable of retaining actuating rods 65 for semi-circular movement about virtual center 66 can be utilized.

Placement of virtual center 66 is generally dictated by the desired force-ratio that is achieved at a given point along the semi-circular stroke of an associated valve-actuating-button 25. Placement of virtual center 66 can be such that this force-ratio will increase, or it will decrease, as a button 25 travels, depending upon the location of virtual center 66. Further force ratio refinement can be achieved by shaping the two ends of actuating rods 65 whereat the rods physically contact a button 25 or a valve stem 18.

In one embodiment of the invention, a force-ratio was provided wherein the ratio of the button-force to the valve-actuating-force was 0.74-to-1 when button movement first began, and was 1-to-1 at the end of the button's semi-circular stroke.

In another embodiment of the invention each of the two actuator rods 65 moved through a semi-circular angle of 45 degrees around virtual center 66. In this embodiment of the invention the above-mentioned force-ratio varied as shown in the following Table-1.

TABLE 1

| Angle of movement | Force-ratio |
| --- | --- |
| 0 degrees | 0.77-to-1 |
| 7.5 degrees | 0.77-to-1 |
| 15.0 degrees | 0.77-to-1 |
| 16.0 degrees | 0.77-to-1 |
| 22.5 degrees | 0.77-to-1 |
| 30.0 degrees | 0.77-to-1 |
| 31.0 degrees | 1.28-to-1 |
| 37.5 degrees | 1.28-to-1 |
| 45.0 degrees | 1.28-to-1 |

Note that in the above embodiment of the invention the force-ratio changes abruptly between 30 degrees and 31 degrees of movement, this being an example of the versatility of the invention.

In yet another embodiment of the invention wherein each of the two actuator rods 65 moved through a semi-circular angle of 45 degrees around virtual center 66 the above-mentioned force-ratio varied as shown in the following Table-2.

TABLE 2

| Angle of movement | Force-ratio |
| --- | --- |
| 0 degrees | 1.0-to-0.95 |
| 7.5 degrees | 1.0-to-0.97 |
| 15.0 degrees | 1-to-1 |
| 16.0 degrees | 1-to-1 |
| 22.5 degrees | 1.0-to-1.02 |
| 30.0 degrees | 1.0-to-1.05 |
| 31.0 degrees | 1.0-to-1.05 |
| 37.5 degrees | 1.0-to-1.07 |
| 45.0 degrees | 1.0-to-1.10 |

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having", as used in the specification, including the claims, shall have the same meaning as the word "comprising."

What is claimed is:

1. A syringe comprising:

a hollow and elongated handle body having a first opening at a bottom thereof, having second opening at a top thereof, and having at least one manually operable and linearly moveable valve operating button at the top thereof;

an insert located within the top of the handle body in general alignment with the second opening in the handle body, the insert having an elongated cavity facing the first opening, and having at least one flow channel connecting the elongated cavity to a bottom portion of the insert;

an elongated nozzle having one end mounted within the elongated cavity, and having an opposite end extending out of the second opening in the handle body;

an elongated valve body mounted within the handle body, the valve body having at least one hose connection at a bottom end thereof, having at least one normally closed and linearly movable valve located at a top end thereof, and having at least one flow channel whose bottom end connects to the hose connection and whose top end connects to the at least one valve, the at least one valve being generally coincident with the bottom portion of the insert; and at least one arcuate-shaped valve actuator rod movably mounted within the insert, the at least one actuator rod having a top end associated with the button and having a bottom end associated with the valve, such that manual depression of the at least one button causes linear movement of the button, arcuate movement of the at least one actuator rod, and linear movement of the at least one valve to an open position.

2. The syringe of claim 1 including alignment means associated with the valve body and the handle body for providing positional alignment between the at least one valve and the bottom end of the actuator rod.

3. The syringe of claim 1 wherein the handle body extends in a first direction, wherein the nozzle extends in a direction that is generally perpendicular to the first direction, wherein the at least one normally closed valve is movable in the first direction to the open position, and wherein the at least one button is movable in a direction that is inclined to the first direction.

4. The syringe of claim 1 wherein the insert includes at least one semi-circular channel having a top end associated with the at least one button and having a bottom end associated with the at least one valve, and wherein the at least one actuator rod is a semi-circular rod that is movably located within the semi-circular channel.

5. The syringe of claim 4 wherein the semi-circular rod is movable in a semi-circle having a virtual center of rotation that is located in a space that need not include any portion of the syringe.

6. The syringe of claim 5 wherein the virtual center of rotation, the at least one semi-circular channel, and the at least one semi-circular rod are constructed and arranged to provide a predetermined button-force to valve-actuating-force ratio.

7. The syringe of claim 6 including alignment means associated with the valve body and the handle body for providing positional alignment between the at least one valve and the bottom end of actuator rod.

8. The syringe of claim 1 including:

at least one tapered bore at the top of the at least one channel of the valve body and extending in a first direction, the at least one tapered bore having a large diameter portion thereof located adjacent to the top of the at least one channel of the valve body, and having a small diameter portion thereof that is spaced from the top of the at least one channel of the valve body;

at least one elongated valve stem located in the at least one tapered bore with a top end thereof associated with the bottom end of at least one arcuate-shaped valve actuator rod;

a ring-shaped valve seat secured to and surrounding the at least one valve stem, the valve seat having an upper surface and a lower surface;

a valve seat O-ring located between the valve seat and the small diameter portion of the at least one tapered bore;

a valve O-ring fixed to a bottom end of the at least one valve stem for engagement with the lower surface of the valve seat; and a compression spring having an upper end fixed to the at least one valve stem and having a lower end engaging the upper surface of the valve seat, to thereby provide a normally closed condition of the at least one valve by force-biasing the valve O-ring into engagement with the lower surface of the valve seat.

9. The syringe of claim 8 wherein the insert includes a semi-circular channel having a top end associated with the at least one button and having a bottom end associated with the at least one valve, and wherein the at least one actuator rod is a semi-circular rod that is movably located within the semi-circular channel.

10. The syringe of claim 9 wherein the semi-circular rod is movable in a semi-circle having a virtual center of rotation that is located in a space that need not include portions of the syringe.

11. The syringe of claim 10 wherein the virtual center of rotation, the at least one semi-circular channel, and the at least one semi-circular rod are constructed and arranged to provide a predetermined button-force to valve-actuating-force ratio.

12. The syringe of claim 1 wherein the insert is formed of brass, and wherein the handle body is formed of aluminum, to thereby provide a syringe that is optimally weight-balanced for use in the human hand.

13. The syringe of claim 12 wherein the aluminum handle body is anodized to provide a desired color.

14. The syringe of claim 13 including alignment means associated with the valve body and the handle body for providing positional alignment between the at least one valve and the bottom end of actuator rod.

15. The syringe of claim 1 including:

a removable insert assembly pin extending through a hole in the handle body and a hole in the insert, the insert assembly pin for removably securing the insert within the handle body.

16. The syringe of claim 15 wherein the nozzle is removably secured in the elongated cavity by a torsion spring secured to the insert, wherein the nozzle is positioned within the torsion spring such that when no rotational unwinding force is applied to the tension spring, the tension spring compresses around the nozzle thereby securing the nozzle to the insert.

17. The syringe of claim 16 including:

means associated with the nozzle and the handle body for resisting rotation of the nozzle about an axis of the elongated cavity.

18. The syringe of claim 1 wherein the nozzle is removably secured in the elongated cavity by a torsion spring secured to the insert, wherein the nozzle is positioned within the torsion spring such that when no rotational unwinding force is applied to the tension spring, the tension spring compresses around the nozzle thereby securing the nozzle to the insert.

19. The syringe of claim 18 including alignment means associated with the valve body and the handle body for providing positional alignment between the at least one valve and the bottom end of actuator rod.

* * * * *